(12) United States Patent
Honicker (10) Patent No.: US 11,071,486 B2
(45) Date of Patent: Jul. 27, 2021

(54) SYSTEM AND METHOD FOR GENERATING ACTIVATION TIMING MAPS (71) Applicant: St. Jude Medical, Cardiology Division, Inc., St. Paul, MN (US)

(72) Inventor: Myles Honicker, Jackson, MS (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 228 days.

(21) Appl. No.: 16/407,413

(22) Filed: May 9, 2019

(65) Prior Publication Data

US 2019/0365262 A1  Dec. 5, 2019

Related U.S. Application Data (60) Provisional application No. 62/679,407, filed on Jun. 1, 2018.

(51) Int. Cl.
*A61B 5/283* (2021.01)
*A61B 5/00* (2006.01)
*A61B 5/339* (2021.01)

(52) U.S. Cl.
CPC .............. *A61B 5/283* (2021.01); *A61B 5/339* (2021.01); *A61B 5/6852* (2013.01); *A61B 5/7221* (2013.01)

(58) Field of Classification Search
CPC ....... A61B 5/283; A61B 5/339; A61B 5/6852; A61B 5/7221
See application file for complete search history.

(56) References Cited

U.S. PATENT DOCUMENTS

| | | | |
|---|---|---|---|
| 5,697,377 A | 12/1997 | Wittkampf | |
| 5,983,126 A | 11/1999 | Wittkampf | |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,263,397 B2 | 8/2007 | Hauck et al. | |
| 7,885,707 B2 | 2/2011 | Hauck | |
| 2007/0073179 A1* | 3/2007 | Afonso ................. | A61B 5/316 600/523 |
| 2014/0371808 A1* | 12/2014 | Ghosh .................. | A61N 1/3682 607/28 |

* cited by examiner

*Primary Examiner* — William J Levicky
*Assistant Examiner* — Naveed R. Kolia
(74) *Attorney, Agent, or Firm* — Wiley Rein LLP (57) ABSTRACT

Cardiac activation timing is mapped using a catheter-mounted roving electrode instead of a fixed (e.g., coronary sinus) electrode. The roving electrode is used to measure an initial electrophysiological signal at an initial cardiac location as a reference signal, which is defined as a reference signal. Local activation time(s) for other cardiac location(s), also measured using the catheter-mounted roving electrode, are determined relative to the reference signal. The stability of the reference signal can be monitored, such as by comparing activation rates or cycle lengths between an instantaneously-measured electrophysiological signal and the initial electrophysiological signal. Smaller differences between the two (e.g., less than about 5%) can be compensated for, while larger differences can result in redefining the reference signal.

16 Claims, 5 Drawing Sheets

SYSTEM AND METHOD FOR GENERATING ACTIVATION TIMING MAPS

CROSS-REFERENCE TO RELATED APPLICATIONS

This application claims the benefit of U.S. provisional application No. 62/679,407, filed 1 Jun. 2018, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for determining local activation times and generating activation timing maps therefrom.

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

Electrophysiology studies can include the creation of a local activation time ("LAT") map. LAT maps can, for example, provide insight to a practitioner as to how an arrhythmia is traveling throughout the cardiac chambers.

Those of skill in the art will recognize that LATs are measured relative to a datum, referred to herein as time zero ("$t_0$"), corresponding to local activation on a reference electrophysiological signal. In many electrophysiology studies, the reference electrophysiological signal is an intracardiac electrogram measured by a stationary reference electrode positioned in the coronary sinus. A coronary sinus signal may not be the most desirable option, however, particularly when mapping complex rhythms.

BRIEF SUMMARY

Disclosed herein is a method of mapping cardiac activation timing, including the steps of: defining an initial electrophysiological signal measured by a catheter-mounted roving electrode at an initial cardiac location as a reference signal, the initial electrophysiological signal having an initial activation rate; and measuring local activation time for a cardiac location other than the initial cardiac location relative to the reference signal using the catheter-mounted roving electrode. A local activation time map can be generated by measuring local activation times for a plurality of cardiac locations other than the initial cardiac location relative to the reference signal using the catheter-mounted roving electrode, and a graphical representation of the local activation time map can be output on a three dimensional cardiac model.

According to aspects of the disclosure, the method also includes monitoring stability of the reference signal, such as by measuring an instantaneous electrophysiological signal using the catheter-mounted roving electrode, the instantaneous electrophysiological signal having an instantaneous activation rate; and computing a difference between the instantaneous activation rate and the initial activation rate. The instantaneous electrophysiological signal can be measured at the initial cardiac location or at a cardiac location other than the initial cardiac location.

It is also contemplated that measuring local activation times for a plurality of cardiac locations other than the initial cardiac location relative to the reference signal using the catheter-mounted roving electrode can include compensating for the difference between the instantaneous activation rate and the initial activation rate. Alternatively or additionally, the method can include redefining the reference signal using the instantaneous electrophysiological signal when the difference between the instantaneous activation rate and the initial activation rate exceeds a preset threshold amount, such as about 5% of the initial activation rate. The preset threshold amount can also be user-adjustable.

Also disclosed herein is a method of mapping cardiac activation timing, including the steps of: introducing an electrophysiology catheter including at least one electrode into a patient's heart; placing the electrophysiology catheter at an initial cardiac location; measuring an initial electrophysiological signal at the initial cardiac location using the at least one electrode; defining the initial electrophysiological signal as a reference signal; moving the electrophysiology catheter to a plurality of locations other than the initial cardiac location; and measuring, at each of the plurality of locations other than the initial cardiac location, a local activation time relative to the reference signal, using the at least one electrode, thereby generating a local activation time map. The method can also include outputting a graphical representation of the local activation time map on a three dimensional cardiac model.

In aspects of the disclosure, the method further includes monitoring stability of the reference signal. For instance, stability of the reference signal can be monitored by: computing a difference between (1) an activation rate of an electrophysiological signal measured at at least one of the plurality of locations other than the initial cardiac location and (2) an activation rate of the initial electrophysiological signal; and, optionally, comparing the computed difference to a preset threshold.

The instant disclosure also provides a system for mapping cardiac activation timing, including a timing reference processor configured to: receive as input a plurality of electrophysiology signals measured by a catheter-mounted roving electrode; define one of the plurality of electrophysiology signals as a reference signal; and determine activation times for others of the plurality of electrophysiological signals relative to the reference signal, thereby generating a local activation time map. The system can further include a display processor configured to output a graphical representation of the local activation time map on a three dimensional cardiac model.

In aspects of the disclosure, the timing reference processor is further configured to monitor stability of the reference signal, and can optionally also be configured to redefine the reference signal when the reference signal exhibits instability.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for the creation of electrophysiology maps (e.g., electrocardiographic maps) that provide information regarding local activation times (e.g., LAT maps). For purposes of illustration, aspects of the disclosure will be described in detail herein in the context of a cardiac mapping procedure carried out using an electrophysiology mapping system (e.g., using an electroanatomical mapping system such as the EnSite Precision™ cardiac mapping system from Abbott Laboratories). More particularly, aspects of the disclosure will be described in the context of generating LAT maps. It is contemplated, however, that the methods, apparatuses, and systems described herein can be utilized in other contexts, such as in the creation of other electrophysiology maps (e.g., conduction velocity maps, peak-to-peak voltage maps, and the like).

Figure 1:
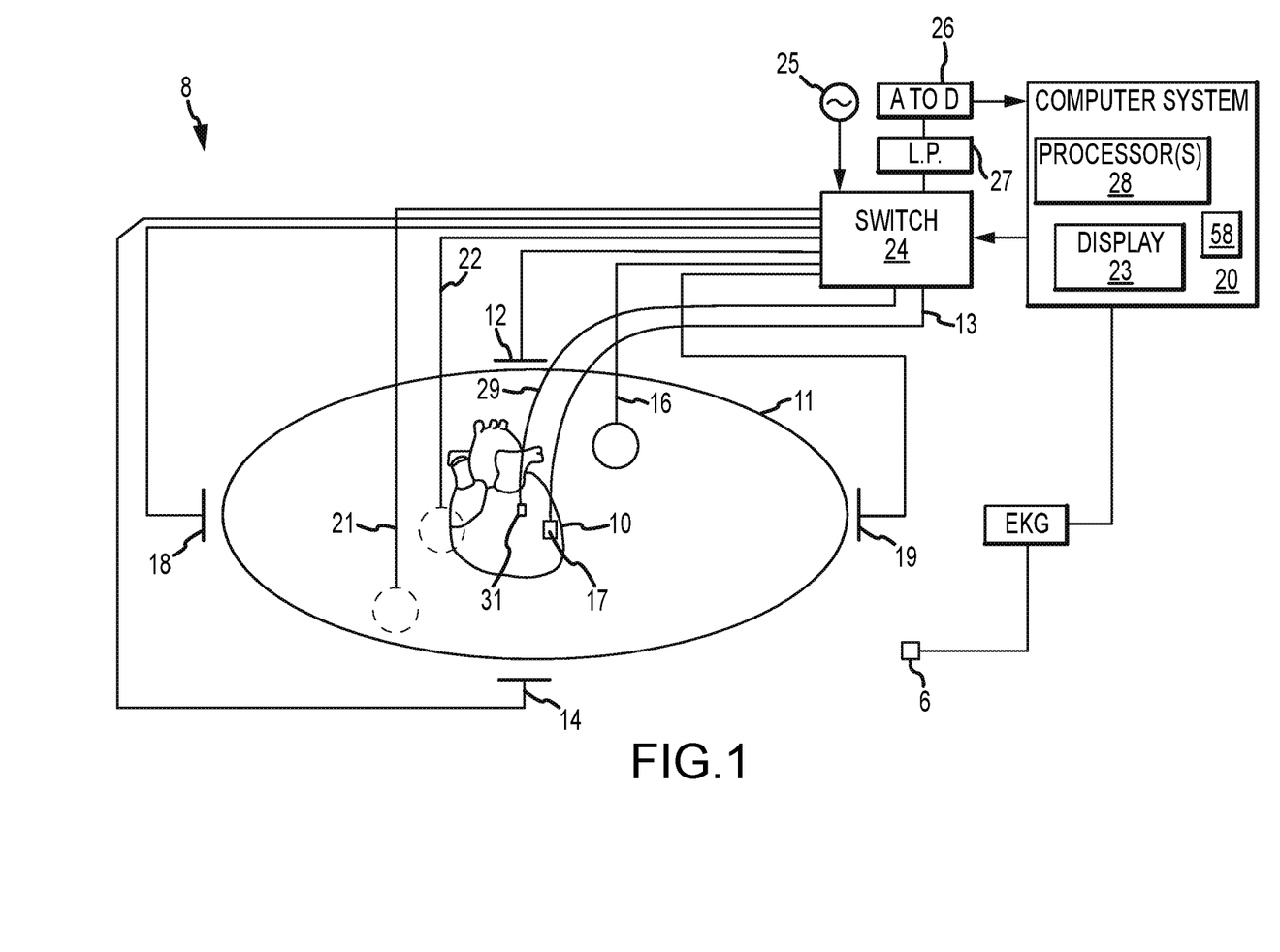
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

The foregoing embodiments are merely exemplary, however, and any number of electrodes and/or catheters may be used. For example, in some embodiments, a high density mapping catheter, such as the Ensite™ Array™ non-contact mapping catheter of Abbott Laboratories, can be utilized.

Figure 2:
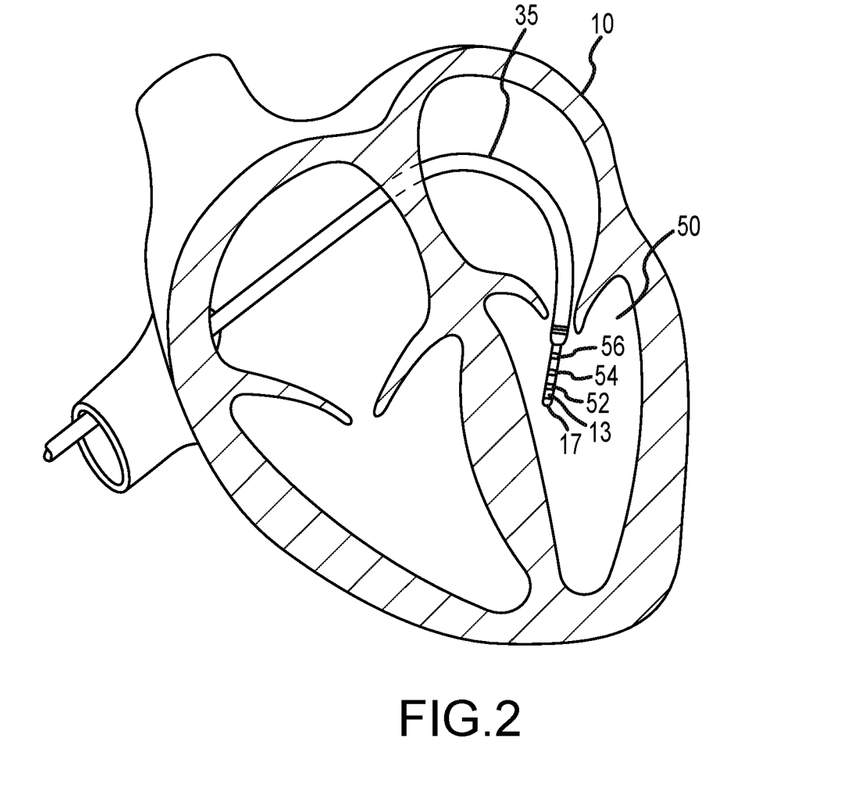
FIG. 2 depicts an exemplary catheter that can be used in connection with aspects of the instant disclosure.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

As discussed above, it is known to use a signal from an electrode 31 as a reference for measuring locations and/or electrophysiological information via electrodes 17, 52, 54, and/or 56 as catheter 13 roves through heart 10. For instance, the location of electrode 31 can be treated as the origin of a three-dimensional coordinate system, and the LAT at electrode 31 can be treated as datum $t_0$ for measurements of LAT's elsewhere on heart 10.

Circumstances are also known, however, where the electrophysiological signal at electrode 31 may not be the most desirable choice of reference signal. For example, the electrophysiological signal at electrode 31 may be difficult to detect consistently, unstable, and/or disassociated from or dissimilar to the rhythm or arrhythmia of interest.

To address these circumstances, aspects of the disclosure relate to utilizing an electrophysiological signal measured by a roving electrode (e.g., 17, 52, 54, 56) carried by catheter 13 as a reference signal in lieu of the electrophysiological signal measured by electrode 31. For example, aspects of the disclosure relate to determining LATs relative to such a reference signal and generating LAT maps therefrom.

Accordingly, system 8 can also include a timing reference module 58. Timing reference module 58 can be used, inter alia, to define a reference signal from a roving electrode (e.g., 17, 52, 54, 56) on catheter 13 and to determine LATs relative to the reference signal as electrodes 17, 52, 54, 56 move through heart 10.

Figure 3:
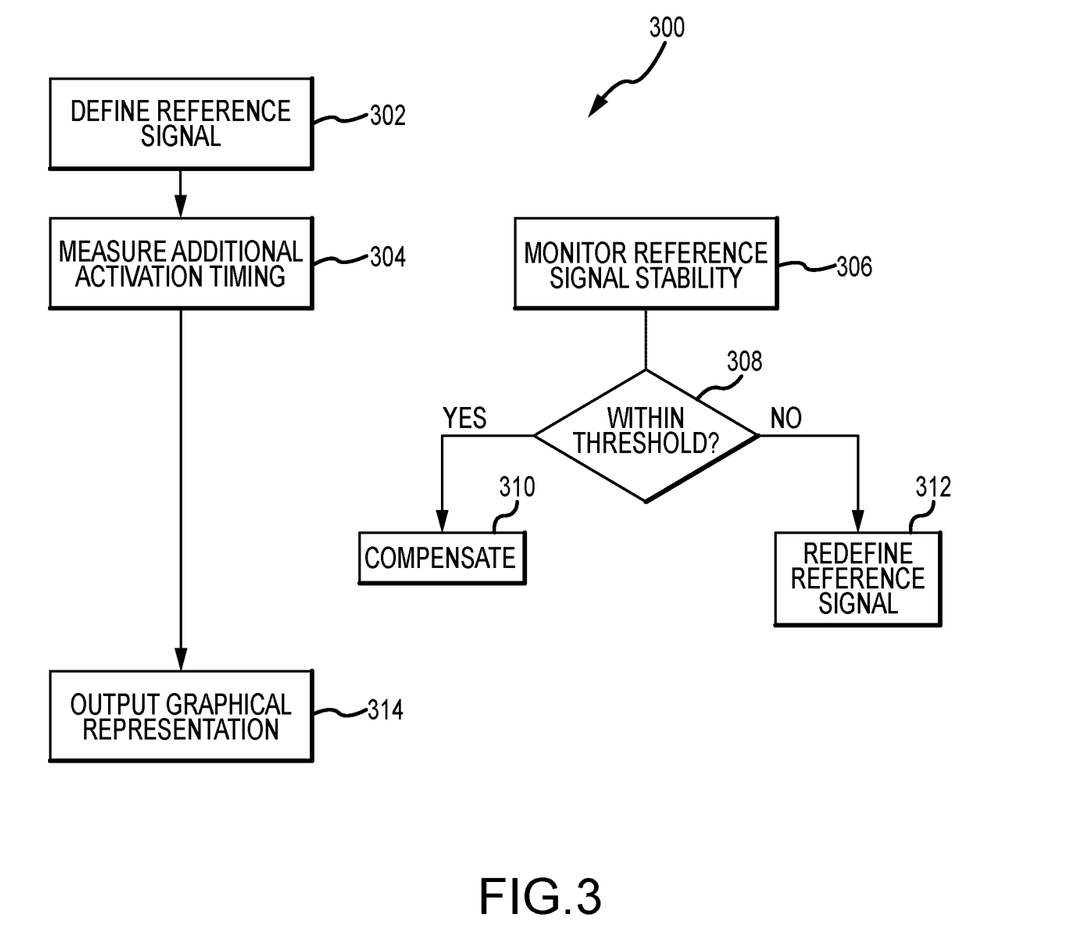
FIG. 3 is a flowchart of representative steps that can be followed according to exemplary embodiments disclosed herein.

One exemplary method of determining LATs and generating an LAT map therefrom according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or timing reference module 58). It should be understood that the representative steps described below can be either hardware- or software-implemented. For the sake of explanation, the term "signal processor" is used herein to describe both hardware- and software-based implementations of the teachings herein.

In block 302, an initial electrophysiological signal, measured at an initial cardiac location, is defined as a reference signal. As described above, this initial electrophysiological signal is not measured by a stationary reference electrode (e.g., it is not measured by reference electrode 31 on catheter 29), but rather by a roving electrode (e.g., electrode 17, 52, 54, and/or 56 on catheter 13). According to aspects of the disclosure, the local activation on the reference signal serves as the datum $t_0$ relative to which LATs at other cardiac locations are measured.

To be a suitable reference signal, the initial electrophysiological signal should be stable and synchronized with the rhythm or arrhythmia of interest. According to aspects of the disclosure, stability and synchronization can be defined with respect to variations in cycle length, with variations of about±5% in the cycle length of the initial electrophysiological signal permissible. The range of acceptable or permissible variability can also be measured in absolute terms (e.g., ±20 ms from the cycle length of the initial electrophysiological signal), rather than in relative terms. It should also be understood that the range of acceptable or permissible variability can be user defined, such as by adjusting a slider or other suitable control through a graphical user interface generated by system 8 and output on display 23.

Advantageously, however, the instant teachings allow any location within the heart to serve as the initial cardiac location instead of constraining it to, for example, the coronary sinus. It should be understood, however, that a fixed reference electrode (e.g., coronary sinus electrode 31) can still be utilized as a geometric reference (that is, as the origin of a three dimensional coordinate system), even if it is not used as the electrophysiological reference (that is, as the datum for electrophysiological measurements).

In block 304, LATs for one or more cardiac locations other than the initial cardiac location are measured. As those of ordinary skill in the art will appreciate, electrophysiological signals are measured (in familiar fashion) by roving electrodes 17, 52, 54, 56 on catheter 13. Those of ordinary skill in the art will also appreciate how to determine LATs from these measured signals. In contrast to existing methods of computing LATs, however, which typically rely on a fixed reference signal (e.g., a coronary sinus electrogram or surface ECG signal), the datum for computing activation timing in block 304 is the LAT $t_0$ of the reference signal defined in block 302. Thus, if a given cardiac location exhibits a local activation before the initial cardiac location, it will have a negative LAT ($t_{LA} < t_0$); conversely, if a given cardiac location exhibits a local activation after the initial cardiac location, it will have a positive LAT ($t_{LA} > t_0$). A collection of a plurality of LATs is referred to herein as an "LAT map."

In block 306, which can occur in parallel to block 304, system 8 (e.g., timing reference module 58) monitors the stability of the reference signal defined in block 302 to ensure that it remains a viable datum for computing LATs elsewhere on heart 10. In aspects of the disclosure, the stability of the reference signal is monitored using activation rates. More particularly, system 8 (e.g., timing reference module 58) computes the difference between the activation rate of the then-current signal measured by a roving electrode 17, 52, 54, 56 (referred to herein as the "instantaneous activation rate"), which can be measured at any cardiac location including the initial cardiac location, and the activation rate of the reference signal defined in block 302 (referred to herein as the "initial activation rate").

Those of ordinary skill in the art will appreciate that cardiac activation rates are not consistent, but rather may vary over time. It is not the case, however, that a deviation from the initial activation rate renders the reference signal unsuitable. Rather, it is contemplated that as long as the difference between the instantaneous activation rate and the initial activation rate does not exceed a preset threshold (decision block 308), the deviation can be compensated for (block 310) when measuring LATs in block 304. Similar to the discussion of stability and synchronization above, the threshold can be expressed in either relative terms (e.g., a variation of about±5%) or absolute terms (e.g., a variation of about±20 ms), and may be user-defined. For instance, the difference between the instantaneous activation rate and the initial activation rate can be added to or subtracted from the end of the acquisition interval, as applicable.

On the other hand, if the difference does exceed the preset threshold, then the reference signal can be redefined (block 312), creating a new $t_0$ on a going forward basis. For instance, if the instantaneous electrophysiological signal is stable and synchronized, it can be used as a new reference signal, replacing the reference signal original defined in block 302.

Another possible circumstance is that the difference between the instantaneous activation rate and the initial activation rate substantially exceeds the preset threshold—for example, the instantaneous activation rate might be two or three times the initial activation rate. System 8 (e.g., timing reference module 58) can interpret this as a discontinuity in the cardiac activation wavefront, such as might occur when inadvertently detecting far-field ventricular activations. In such instances, the faster activation rate can be ignored.

In block 314, a graphical representation of the LAT map can be output, for example, on a three dimensional cardiac model displayed on display 23.

Figure 4A:
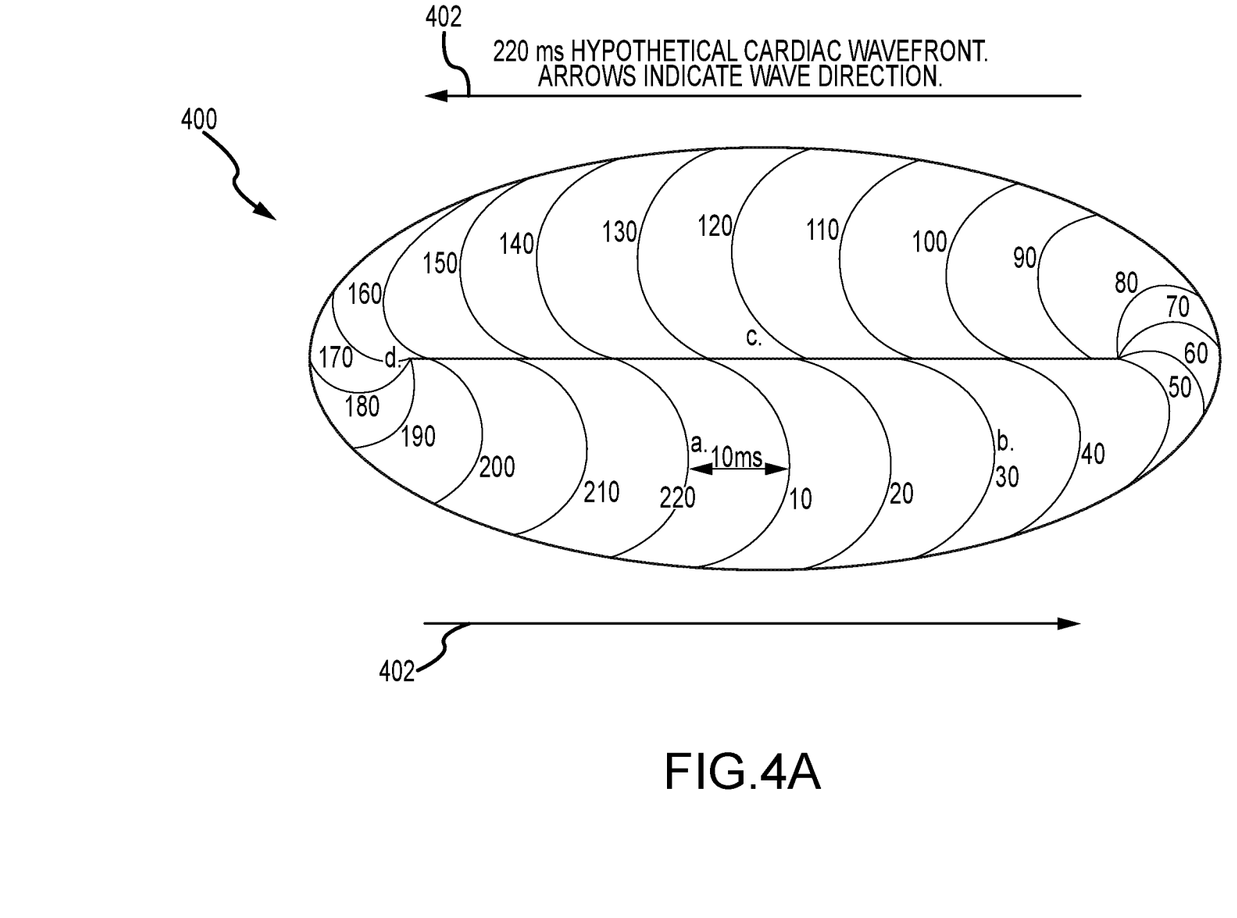
FIG. 4A depicts a hypothetical 220 ms cardiac activation wavefront.
Figure 4B:
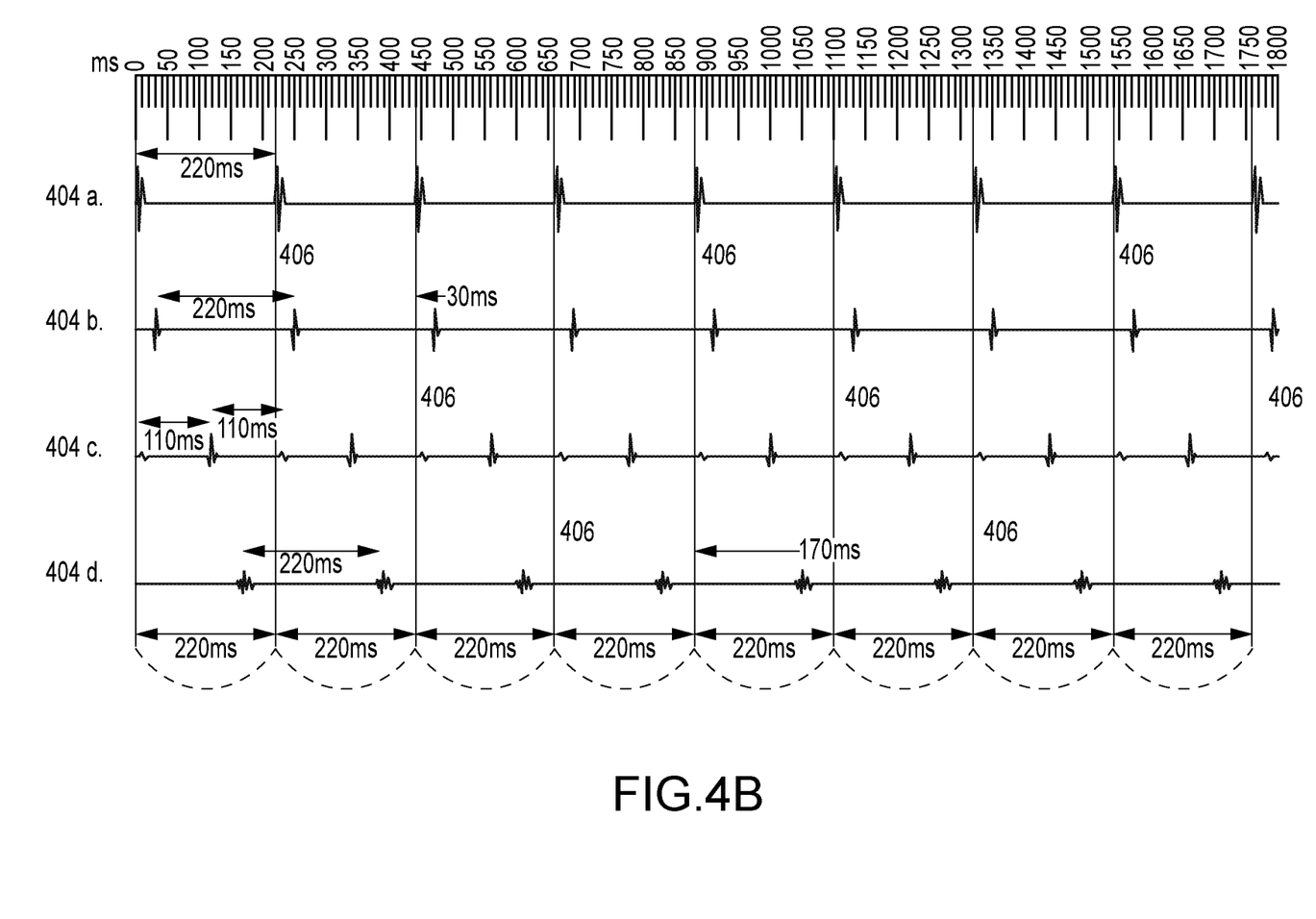
FIG. 4B depicts hypothetical electrograms measured at a series of points along the hypothetical cardiac activation wavefront of FIG. 4A.

Aspects of the disclosure can also be understood with reference to FIGS. 4A and 4B. FIG. 4A depicts a hypothetical cardiac activation wavefront 400, which proceeds in the direction of arrows 402 (i.e., counterclockwise). Four points, "a," "b," "c," and "d," are annotated on wavefront 400. FIG. 4B shows the corresponding electrograms 404a, 404b, 404c, and 404d measured by a roving catheter (e.g., catheter 13) at points a-d.

As shown in FIG. 4B, electrogram 404a measured at point a has a cycle length of about 220 ms. This is also reflected in the activation isochrones shown in FIG. 4A, which are provided in 10 ms increments. If electrogram 404a is selected as the reference signal, therefore, activation at point a becomes the datum $t_0$ relative to which LATs at other cardiac locations are measured. The datum $t_0$ is shown with dashed vertical lines 406 in FIG. 4B.

As shown in FIG. 4B, electrogram 404b measured at point b also has a cycle length of about 220 ms. As will be apparent from both FIG. 4B and the isochrones of FIG. 4A, however, activation at point b is about 30 ms after activation at point a. Thus, measured relative to $t_0$, the LAT at point b is about 30 ms. Further, electrogram 404a remains a viable reference signal for measuring LATs at point b as long as the cycle length at point b does not deviate from the cycle length at point a by more than about 5%.

Electrogram 404c demonstrates that point c is experiencing discontinuous activation. More particularly, electrogram 404c shows that point c undergoes two activations for every activation at point a, with electrogram 404c exhibiting a minor deflection substantially simultaneous with activation at point a, and a major deflection about 110 ms after activation at point a. The interval between deflections of like type, however, is still about 220 ms. Thus, electrogram 404a remains a viable reference signal for measuring LATs at point c.

Finally, electrogram 404d measured at point d also has a cycle length of about 220 ms. As will be apparent from both FIG. 4B and the isochrones of FIG. 4A, however, activation at point d is about 170 ms after activation at point a. Thus, measured relative to $t_0$, the LAT at point d is about 170 ms. Further, electrogram 404a remains a viable reference signal for measuring LATs at point d as long as the cycle length at point d does not deviate from the cycle length at point a by more than about 5%.

Further, because electrograms 404b, 404c, and 404d exhibit generally constant LATs relative to electrogram 404a (that is, they are stabilized and synchronized with respect to the rhythm or arrhythmia of interest), any of them would be suitable reference signals. For instance, if a practitioner chose to redefine the reference signal to correspond to electrogram 404b, the new $t_0$ would be about 30 ms to the right of the original $t_0$. The practitioner could then choose to redefine the reference signal to correspond to electrogram 404c, moving $t_0$ another about 80 ms to the right. Finally, the practitioner could choose to redefine the reference signal to correspond to electrogram 404d, moving $t_0$ still further about 60 ms to the right. In this manner, the practitioner can achieve a "virtual leapfrog" technique to mapping LATs.

Although several embodiments have been described above with a certain degree of particularity, those skilled in the art could make numerous alterations to the disclosed embodiments without departing from the spirit or scope of this invention.

For example, the teachings herein can be applied in real time (e.g., during the collection of electrophysiology data points as part of an electrophysiology study) or during post-processing (e.g., upon a stored collection of electrophysiology data points that were collected during a prior electrophysiology study).

As another example, the teachings herein can be applied to any procedure where a timing reference is required, such as for ventricular blanking of far field signals during acquisition of sequential atrial points.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac activation timing, comprising:
    defining an initial electrophysiological signal measured by a catheter-mounted roving electrode at an initial cardiac location as a reference signal, the initial electrophysiological signal having an initial activation rate; and
    measuring local activation time for a cardiac location other than the initial cardiac location relative to the reference signal using the catheter-mounted roving electrode.

2. The method according to claim 1, wherein measuring local activation for a cardiac location other than the initial cardiac location relative to the reference signal using the catheter-mounted roving electrode comprises measuring local activation times for a plurality of cardiac locations other than the initial cardiac location relative to the reference signal using the catheter-mounted roving electrode, thereby generating a local activation time map.

3. The method according to claim 2, further comprising outputting a graphical representation of the local activation time map on a three dimensional cardiac model.

4. The method according to claim 2, further comprising monitoring stability of the reference signal.

5. The method according to claim 4, wherein monitoring stability of the reference signal comprises:
    measuring an instantaneous electrophysiological signal using the catheter-mounted roving electrode, the instantaneous electrophysiological signal having an instantaneous activation rate; and
    computing a difference between the instantaneous activation rate and the initial activation rate.

6. The method according to claim 5, wherein the instantaneous electrophysiological signal is measured at the initial cardiac location.

7. The method according to claim 5, wherein the instantaneous electrophysiological signal is measured at a cardiac location other than the initial cardiac location.

8. The method according to claim 5, wherein measuring local activation times for a plurality of cardiac locations other than the initial cardiac location relative to the reference signal using the catheter-mounted roving electrode further comprises compensating for the difference between the instantaneous activation rate and the initial activation rate.

9. The method according to claim 5, further comprising redefining the reference signal using the instantaneous electrophysiological signal when the difference between the instantaneous activation rate and the initial activation rate exceeds a preset threshold amount.

10. The method according to claim 9, wherein the preset threshold amount is 5% of the initial activation rate.

11. The method according to claim 9, wherein the preset threshold amount is user-adjustable.

12. A method of mapping cardiac activation timing, comprising:
 introducing an electrophysiology catheter including at least one electrode into a patient's heart;
 placing the electrophysiology catheter at an initial cardiac location;
 measuring an initial electrophysiological signal at the initial cardiac location using the at least one electrode;
 defining the initial electrophysiological signal as a reference signal;
 moving the electrophysiology catheter to a plurality of locations other than the initial cardiac location; and
 measuring, at each of the plurality of locations other than the initial cardiac location, a local activation time relative to the reference signal, using the at least one electrode, thereby generating a local activation time map.

13. The method according to claim 12, further comprising outputting a graphical representation of the local activation time map on a three dimensional cardiac model.

14. The method according to claim 12, further comprising monitoring stability of the reference signal.

15. The method according to claim 14, wherein monitoring stability of the reference signal comprises computing a difference between (1) an activation rate of an electrophysiological signal measured at at least one of the plurality of locations other than the initial cardiac location and (2) an activation rate of the initial electrophysiological signal.

16. The method according to claim 15, wherein monitoring stability of the reference signal further comprises comparing the computed difference to a preset threshold.

* * * * *